United States Patent
Jones et al.

(10) Patent No.: US 8,785,175 B2
(45) Date of Patent: Jul. 22, 2014

(54) METHODS AND PRODUCTS USED TO GROW AND HARVEST ALGAE

(75) Inventors: William N. Jones, West Point, GA (US); Daniel Price, LaGrange, GA (US); James Hobbs, LaGrange, GA (US)

(73) Assignee: Interface, Inc., Atlanta, GA (US)

( * ) Notice: Subject to any disclaimer, the term of this patent is extended or adjusted under 35 U.S.C. 154(b) by 6 days.

(21) Appl. No.: 13/186,790

(22) Filed: Jul. 20, 2011

(65) Prior Publication Data

US 2012/0018373 A1    Jan. 26, 2012

Related U.S. Application Data

(60) Provisional application No. 61/365,886, filed on Jul. 20, 2010, provisional application No. 61/409,242, filed on Nov. 2, 2010.

(51) Int. Cl.
*C12N 1/12* (2006.01)
*C12M 1/00* (2006.01)
*A01G 7/00* (2006.01)

(52) U.S. Cl.
USPC .................. 435/257.1; 435/283.1; 47/1.4

(58) Field of Classification Search
None
See application file for complete search history.

(56) References Cited

U.S. PATENT DOCUMENTS

| | | | | |
|---|---|---|---|---|
| 3,385,751 A | * | 5/1968 | Willard et al. | 428/94 |
| 3,654,884 A | * | 4/1972 | Dawbarn | 112/410 |
| 4,333,263 A | | 6/1982 | Adey | |
| 4,356,220 A | | 10/1982 | Benedyk | |
| 4,371,576 A | * | 2/1983 | Machell | 428/94 |
| 5,851,398 A | | 12/1998 | Adey | |
| 5,958,527 A | | 9/1999 | Prevost | |
| 6,338,885 B1 | * | 1/2002 | Prevost | 428/17 |
| 2003/0104161 A1 | * | 6/2003 | Edwards | 428/85 |
| 2005/0031803 A1 | * | 2/2005 | Prevost | 428/17 |
| 2007/0275207 A1 | * | 11/2007 | Higgins et al. | 428/95 |
| 2011/0073542 A1 | | 3/2011 | Adey et al. | |

FOREIGN PATENT DOCUMENTS

| | | |
|---|---|---|
| CN | 101284695 | 10/2008 |
| CN | 103108539 | 5/2013 |
| JP | 05344830 | 12/1993 |
| UY | 33524 | 2/2012 |
| WO | 9856992 | 12/1998 |
| WO | 2011038413 | 3/2011 |
| WO | 2012012525 | 1/2012 |

OTHER PUBLICATIONS

PCT/US2011/044672, International Search report and Written Opinion, Sep. 6, 2011, 12 pages.

(Continued)

*Primary Examiner* — Chris R Tate
*Assistant Examiner* — Douglas F White
(74) *Attorney, Agent, or Firm* — Kilpatrick Townsend & Stockton LLP

(57) ABSTRACT

Systems and methods that facilitate the creation and harvesting of algae using tufted products. One exemplary tufted product comprises a substrate and tufts tufted through the substrate. The use of a tufted product provides various advantages with respect to the creation and harvesting of algae. Among other things, such products can be configured to improve the amount of algal-growing surface area provided and other growing environment characteristics and to facilitate the harvesting of the algae from the tufted product by facilitating the release of all or most of the algae from attachment to the tufted product.

15 Claims, 10 Drawing Sheets

(56) References Cited

OTHER PUBLICATIONS

Hydromentia, Algal Turf Scrubber Technology, Jan. 5, 2005, 13 pages.
PCT/US2011/044672, "International Preliminary Report on Patentability", Jan. 31, 2013, 7 pages.
CN201180036337.2, "Office Action", Aug. 14, 2013, 25 pages.
Adey, et al., "Phosphorus Removal from Natural Waters Using Controlled Algal Production," Restoration Ecology, Mar. 1993 (11 pages).
Craggs, et al., "A controlled stream mesocosm for tertiary treatment of sewage," Ecological Engineering Jun. 1996 (pp. 149-169).
Small, et al., "Are Current Estimates of Coral Reef Biodiversity too Low? The View through the Window of a Microcosm," Atoll Research Bulletin, No. 458, Sep. 1998 (21 pages).
Small, et al., "Reef corals, zooxanthellae and free-living algae: a microcosm study that demonstrates synergy between calcification and primary production," Ecologicial Engineering 16 (2001) (pp. 443-457).
Ramey, et al., "Production of Butyric Acid and Butanol from Biomass," U.S. Department of Energy 2004 (103 pages).
Sano, et al., "Economic Analysis of Water Treatments for Phosphorus Removal in Florida," University of Florida, Food and Resource Department, University of Florida, 2004 (7 pages).
Adey, U.S. Appl. No. 61/246,477; "Basal Screen for Enhancing Algal Biomass Production in ATS Systems", filed Sep. 28, 2009, 20 pages.
"Proposal for Suwannee River Water Quality Performance Testing and Development of a Phase 1 Algal Turf Scrubber® (ATS™) System on the Suwannee River," Proposal Prepared for Suwannee River Water Management District, Sep. 2, 2011.
Chinese Patent Application No. 201180036337.2, Second Office Action, issued Jan. 27, 2014, 26 pages.

\* cited by examiner

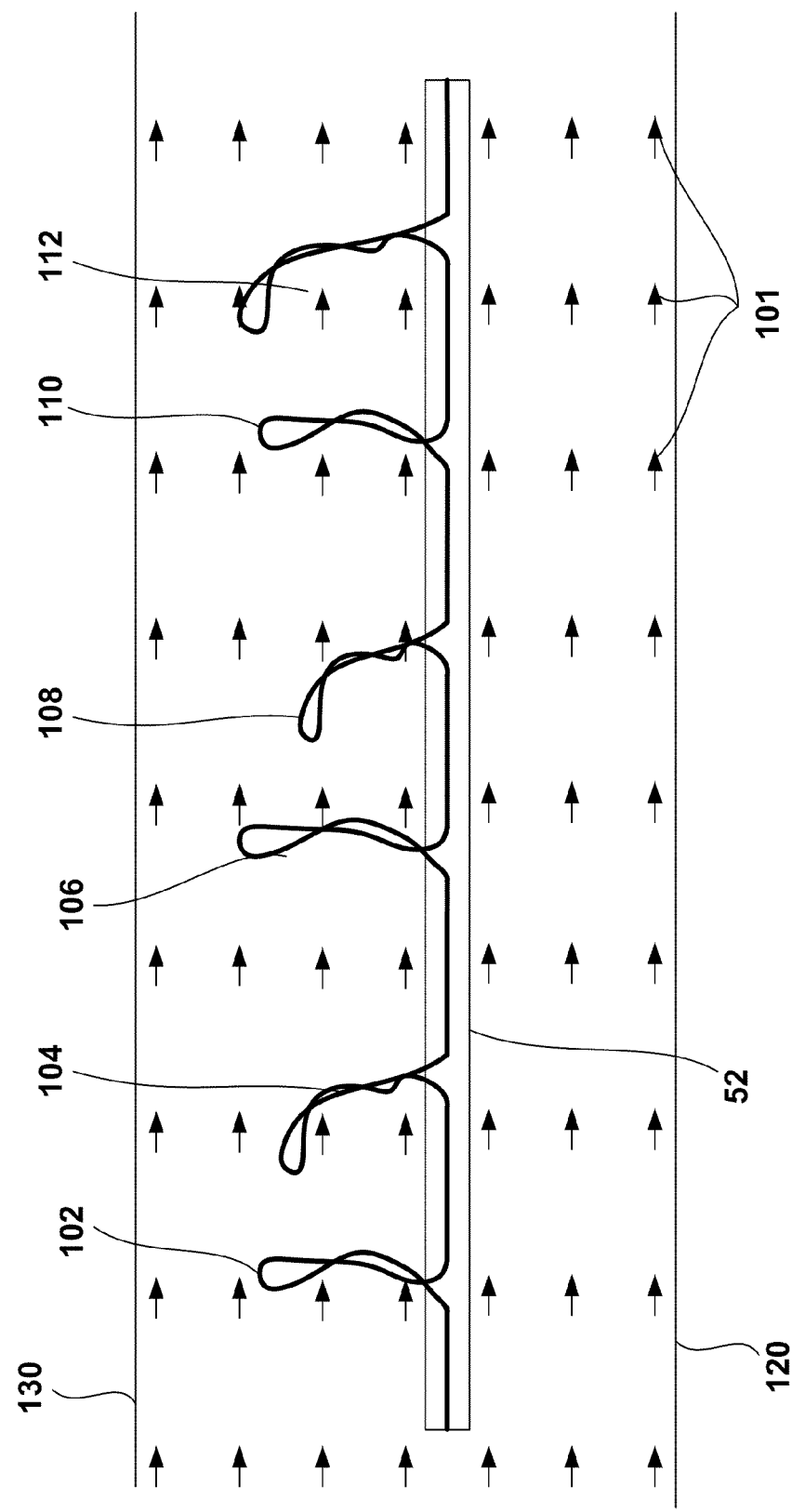

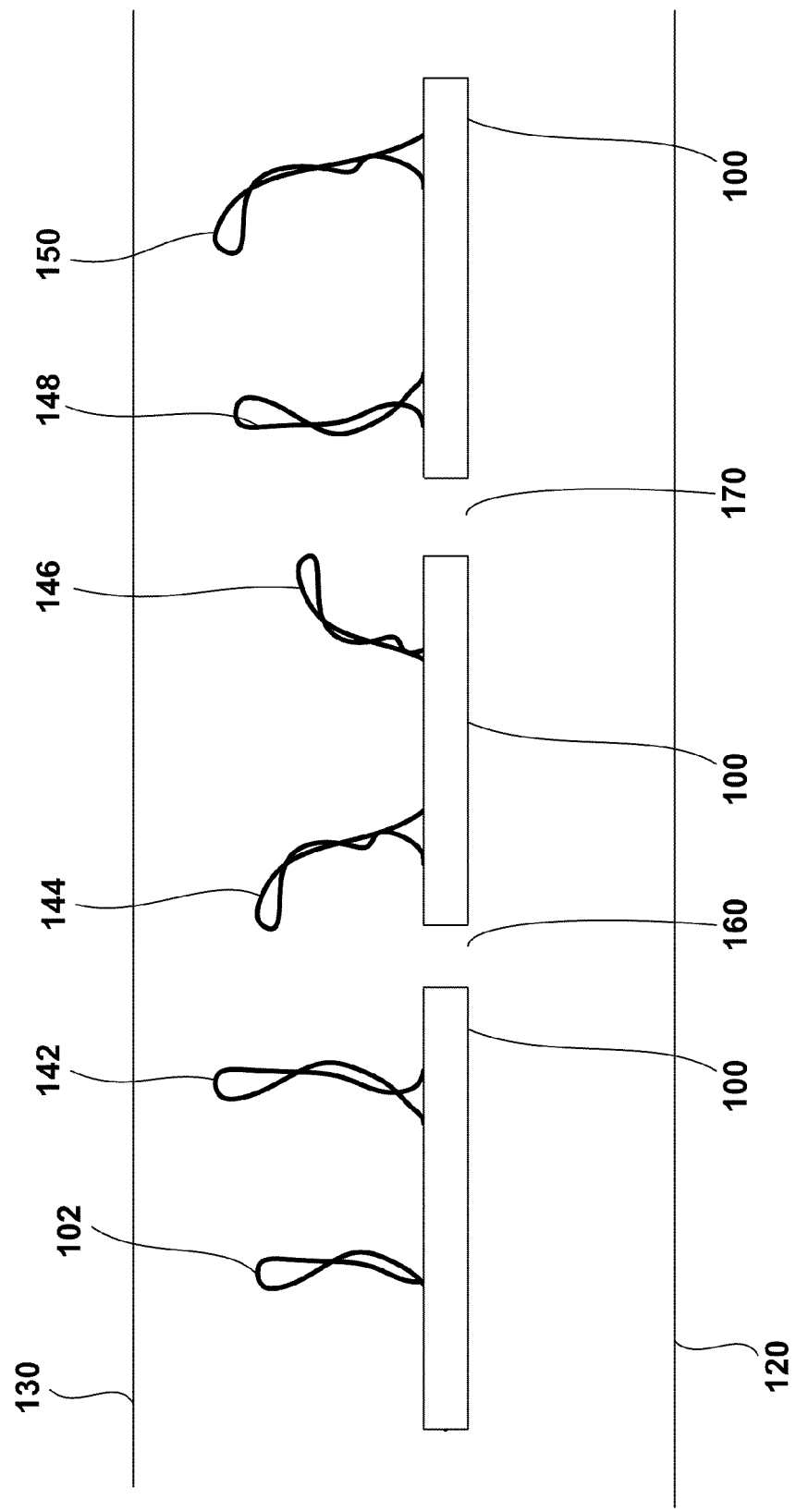

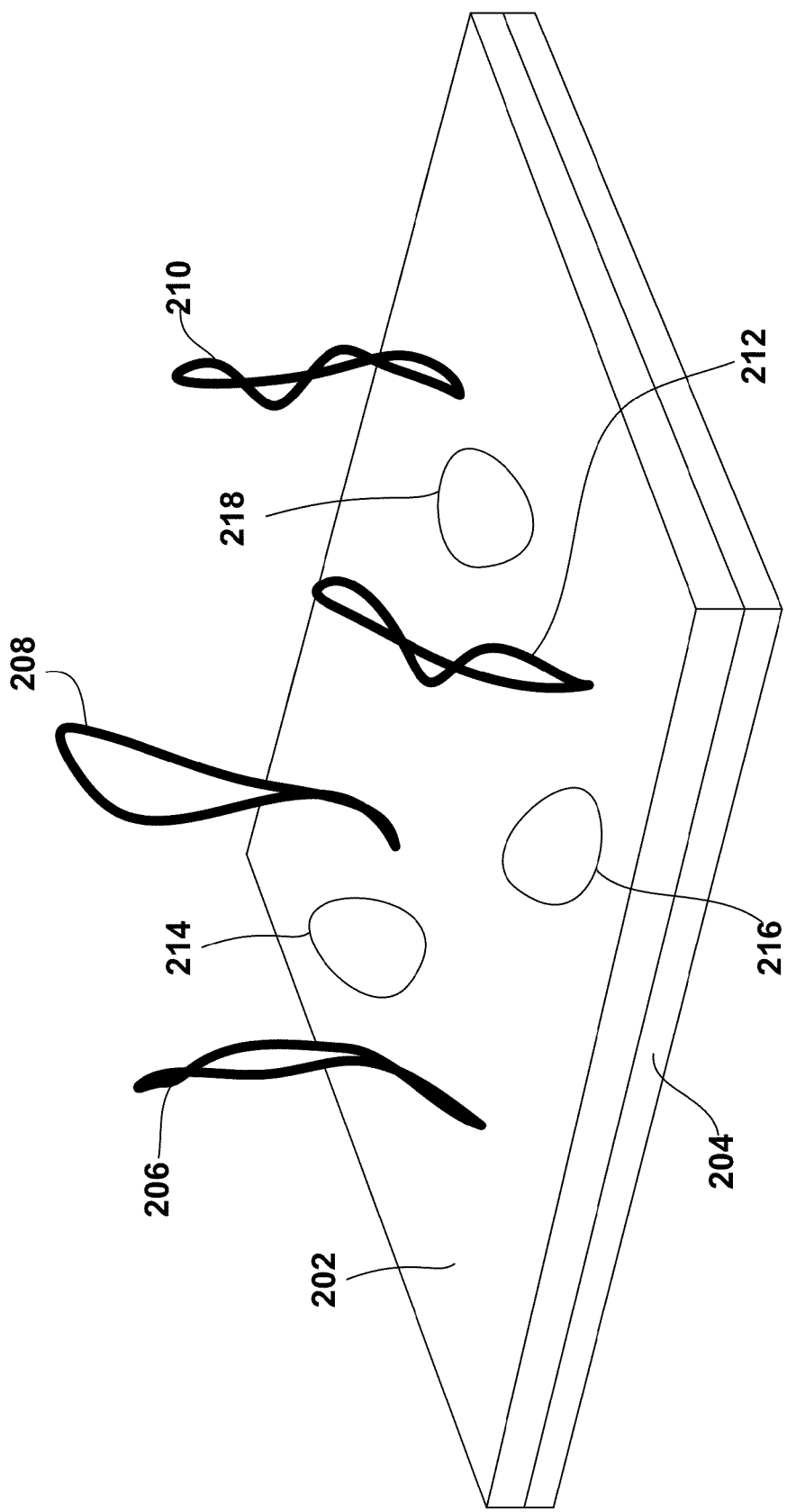

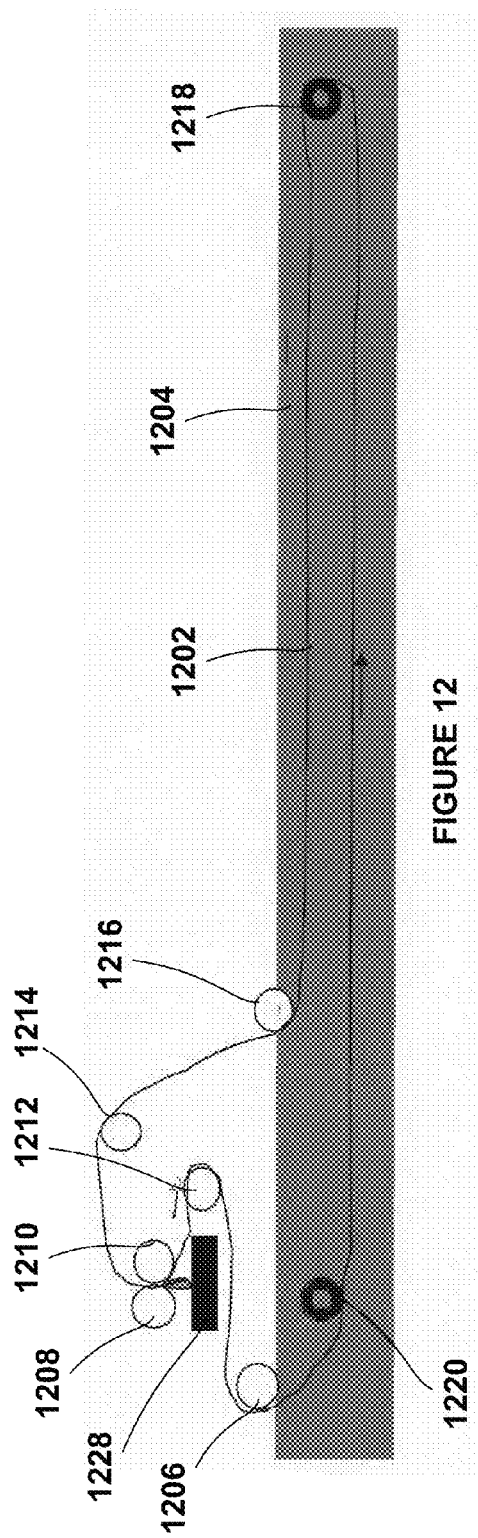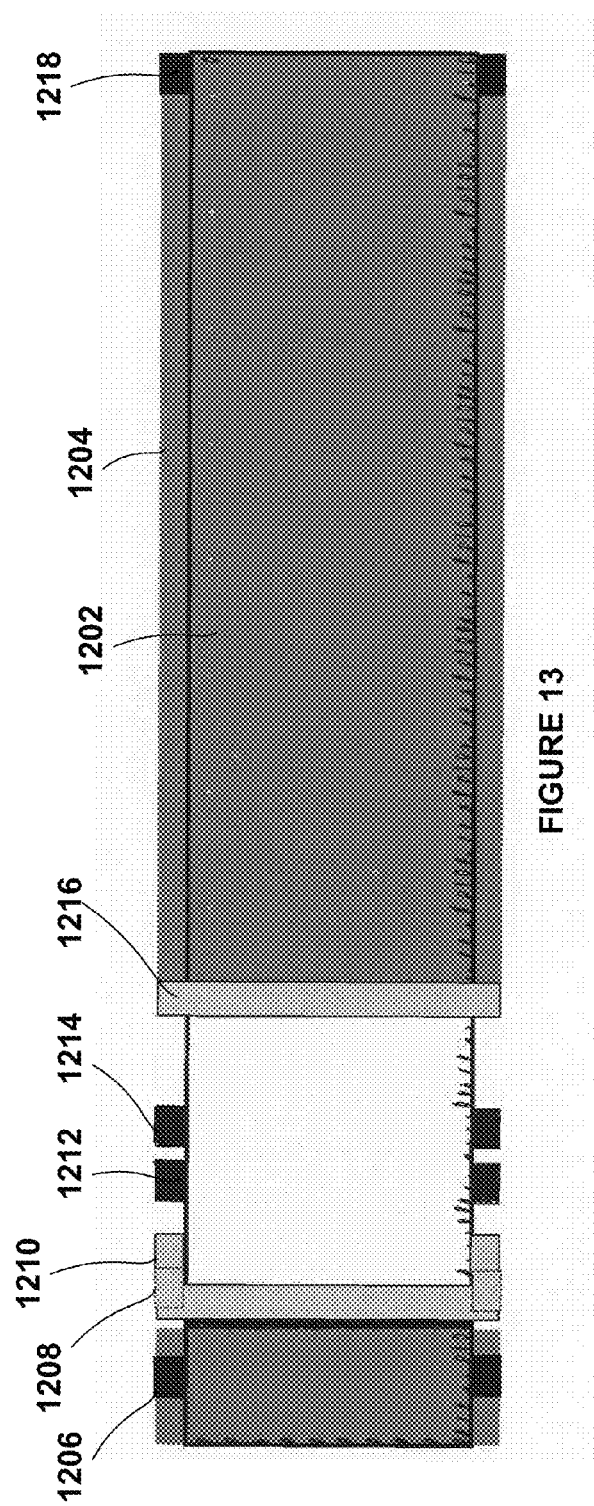

METHODS AND PRODUCTS USED TO GROW AND HARVEST ALGAE

RELATED APPLICATIONS

This application claims the benefit of U.S. Provisional Application Ser. No. 61/365,886 filed Jul. 20, 2010 titled "Products Used to Culture Algae for Remediation and Fuel Production," and U.S. Provisional Application Ser. No. 61/409,242 filed Nov. 2, 2010 titled "Products Used to Culture Algae for Remediation and Fuel Production," the content of both of which are hereby incorporated by reference.

FIELD

Embodiments of this invention generally relate to the growth and/or harvesting of algae and more specifically relate to tufted and other products used for such purposes.

BACKGROUND

Algal turfs have long been known to be efficient scrubbers of carbon dioxide, nutrients, and a variety of pollutants. Algal turfs are also known to produce biomass and oxygen, raise pH, and fix nitrogen. The productivity associated with tropical reefs can be at least partially attributed to the natural presence of algal turf performing one or more of these functions. In practical applications, algal turf scrubbing can be used for a variety of purposes including, but not limited to, filtering aquaria, nutrient and contaminant removal, and in the production of biomass as a fertilizer or food-based energy source.

The science of phycoremediation involves the use of algae to sequester or degrade water borne pollutants. U.S. Pat. No. 4,333,263 (hereinafter "the '263 patent") to Walter H. Adey describes an "Algal Turf Scrubber" and is incorporated herein in its entirety by this reference. The '263 patent describes a method of producing an algal turf for use as a scrubber of carbon dioxide, nutrients and pollutants as well as biomass production. A growing surface, such as a screen, is provided on a water surface and used to grow spores or benthic microalgae. The growing surface is subjected to periodic water surge action to promote metabolite cellular-ambient water exchange and light is provided to promote growth. The '263 patent further describes that the growing turf is harvested before being overgrown by larger macroalgae.

No standardized substrate for algal growth has been developed for industrial phycoremediation application. More generally, products used to culture algae generally provide simple screens that, at least in certain respects, are inefficient and/or ineffective with respect to facilitating and optimizing algal growth. Alternatives to such screens and other traditional substrates that better facilitate improved algae use for bioremediation and fuel production purposes are desired.

BRIEF SUMMARY

The terms "invention," "the invention," "this invention" and "the present invention" used in this patent are intended to refer broadly to all of the subject matter of this patent and the patent claims below. Statements containing these terms should be understood to not limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to the appropriate portions of the entire specification of this patent, any or all drawings and each claim.

This invention relates to facilitating the growth and/or harvesting of algae using tufted products. One exemplary tufted product comprises a substrate and tufts tufted through the substrate. The use of a tufted product provides various advantages with respect to the creation and harvesting of algae. Among other things, such products can be configured to improve the amount of algal-growing surface area provided and other growing environment characteristics and to facilitate the harvesting of the algae from the tufted product by facilitating the release of all or most of the algae from attachment to the tufted product.

The use of a tufted product to facilitate algae growth and removal comprises submersing a tufted product in water, allowing algae to grow for a period of time on the tufted product, and removing at least some of the algae from the tufted product. Embodiments of the tufted products disclosed herein may also be used to reclaim or harvest algae from an algae-infested body of water (e.g., a lake, bay, gulf, ocean, or other natural body of water) to remediate the water in the body of water.

BRIEF DESCRIPTION OF THE DRAWINGS

The specification makes reference to the following appended figures, in which use of like reference numerals in different figures is intended to illustrate like or analogous components.

FIG. 9 is a side cross sectional view showing the portion of the exemplary tufted product of FIG. 8 submerged in flowing water to facilitate algae growth.

FIG. 10 is another side cross sectional view (taken at 90° relative to the view of FIG. 9) showing the portion of the exemplary tufted product of FIG. 8 submerged in flowing water to facilitate algae growth.

FIG. 11 is a top perspective view of a portion of another exemplary tufted product according to embodiments of this invention.

FIG. 12 is a side cross sectional view showing a tufted product used to reclaim algae from an algae-infested body of water to remediate the water in the body of water according to embodiments of this invention.

FIG. 13 is a top view of the tufted product of FIG. 12.

DETAILED DESCRIPTION

Various tufted products can be used to facilitate the growth and/or harvesting of algae. Such tufted products generally comprise a backing material with tufts protruding on one or both sides. Such a backing material is typically a relatively thin, single or multi-layer sheet. Such tufts can be formed of staple or filament yarns protruding as single strand portions, loops, cut-loops, or otherwise and may be made from a variety of natural or synthetic materials. A tufted product used to facilitate the use of algae in bioremediation or fuel production may be formed by hand or by machine. For example, tufts may be formed by hand stitching yarns into a backing material to form the tufts.

A tufting machine can also be used. A tufted product can be produced by tufting fiber with machine and product specifications to improve surface area, nutrient flow, algal growth, and nutrient uptake. Many tufting machines have one or more rows of needles that form tufts using multiple yarns. Each yarn can be fed through a single needle of such a machine and thus used to form a straight or staggered row of tufts along a backing material as the backing material moves through the machine as the tufted product is being created. Tufting gauge, stitch, and yarn size can be selected based on nutrient flow and other requirements appropriate for a given environment and application.

The use of tufting machines to form tufted products for algae growth can similarly provide various advantages. A tufting machine may produce such products more quickly, more accurately, more consistently, more efficiently, and/or less expensively than other methods of forming tufted products and other algae-growing substrates. Moreover, tufting machine parameter settings may be adjusted during the product development process to better test and identify improved product characteristics including, but not limited to, characteristics related to tuft spacing, tuft height, and tuft shift-pattern.

Figure 1:
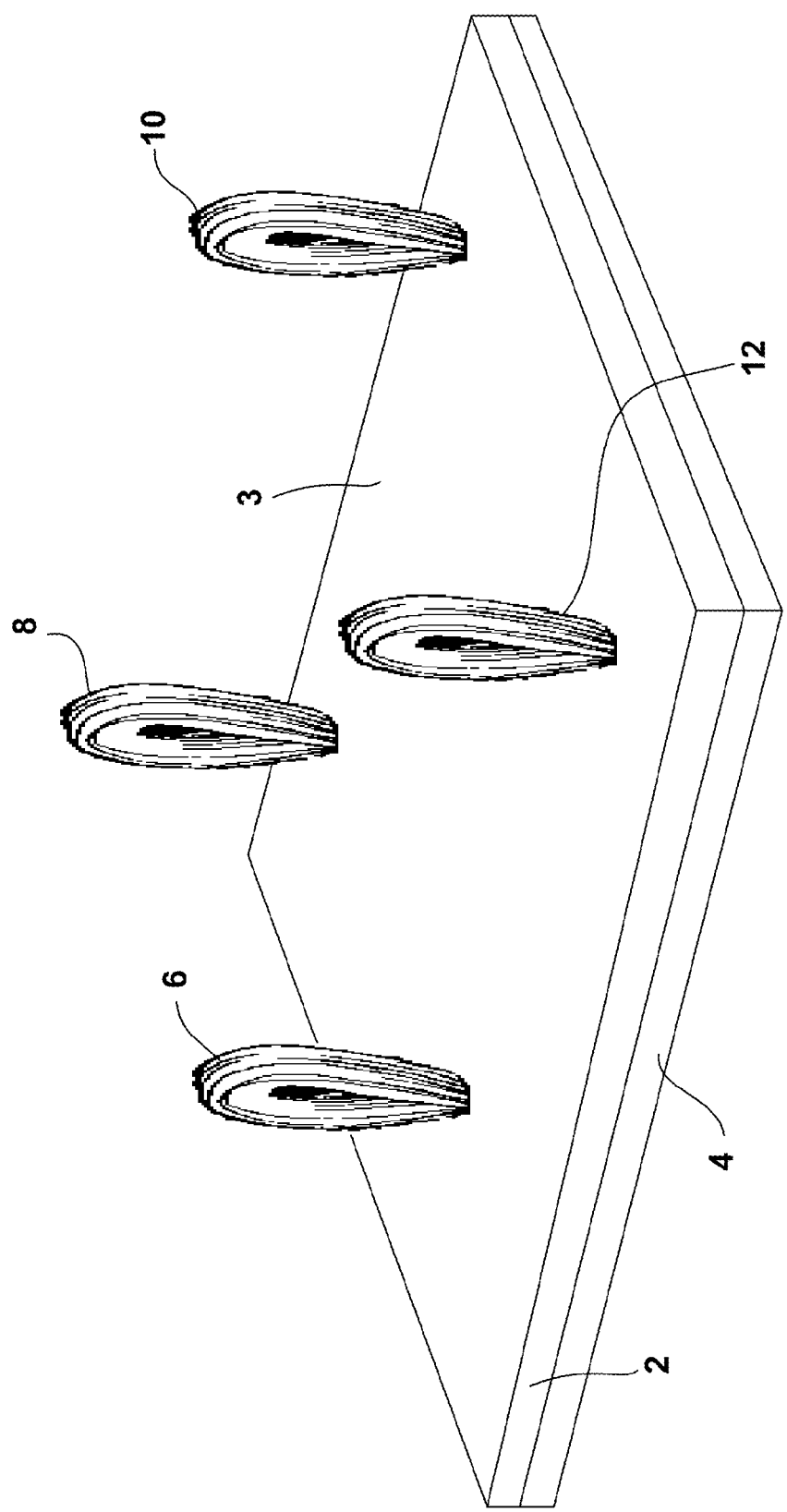
FIG. 1 is a top perspective view of a portion of an exemplary tufted product according to embodiments of this invention.

FIG. 1 is a top perspective view of a portion of an exemplary tufted product configured to harvest algae. The exemplary tufted product comprises a substrate 2 used as a primary backing into which tufts 6, 8, 10, 12 are tufted and protrude from the top side 3 of the substrate 2. Attributes of the substrate 2 into which tufts 6, 8, 10, 12 are formed can be configured to facilitate algae growth and/or removal. In certain embodiments, such a substrate 2 comprises a woven material. Such a woven material may have a non-woven cap (not shown) providing a "fuzzy" surface of small fibers that may further promote algae growth. In other words, the non-woven cap may help provide a surface that facilitates attachment of algae to increase algae and diatom yield. In such embodiments, the non-woven cap would be positioned and exposed on the top side 3 of the surface 2. In some embodiments, it is desirable to avoid using such a non-woven cap to promote removal of algae growth from the tufted product.

Woven polypropylene with or without a non-woven cap coat is an example of a substrate material used as a primary backing in tufted products usable to culture algae for phycoremediation or bio-fuel production. Examples of such material include Polybac® offered by Propex® of Chattanooga, Tenn., available with and without a non-woven cap coat. A woven substrate or a non-woven may be used. A woven substrate may provide greater strength than a non-woven substrate. The color of such a material may facilitate light penetration and/or reflectance. White, tan, or other light colors, for example, may facilitate such functions.

In FIG. 1, hot melt 4 is used to secure the tufts and/or add stability to the tufted product. For example, a polymer-based (EVA, PE or co-polymer) hot melt adhesive can be applied at 18-24 oz/yd$^2$ to the substrate 2 to provide dimensional stability and help secure the tufted stitches. Such a polymer coating may also provide additional strength for water and mechanical stress resistance. Generally, a hot melt 4, secondary backing, or other mechanism may be used to secure tufts in a tufted product to withstand submersion in standing and/or flowing water. Additionally or alternatively, a polypropylene film may be used to lock tufts and strengthen the fabric. Such a film may be applied, for example, by spraying adhesive to the backstitch of the tufted substrate and then sticking the polypropylene film. This may protect the stitch and give the fabric strength. Locking can provide significant benefits with respect to the overall weight, flexibility, and strength of a tufted product for use in collecting, growing, and harvesting algae. Various locking mechanisms are contemplated to bind tufts, enhance performance, and improve long term durability.

In FIG. 1, the illustrated tufts 6, 8, 10, 12 are loops. Tufts 6, 8, 10, 12 in a tufted product configured to culture, harvest, or otherwise collect algae may be loops, cut loops, coiled, or otherwise configured to achieve the particular algae-related objective. Yarn can be tufted to form tufts that provide certain advantages. For example, yarn tufts can be formed into a loop pile, cut pile, or a combination of loop piles and cut piles. In one exemplary embodiment, a product has loop construction that preferably causes a coiling effect in the loops. Such coiling may help minimize impact on nutrient flow while improving surface area. In another exemplary embodiment, a product can have cut piles to improve filamentation of fiber on tips and/or throughout the entire stem for particular algae types.

One particular exemplary tufted product comprises a substrate 2 and air-entangled, white, nylon 6 yarn tufted at ¼ gauge to create open loops 6, 8, 10, 12 between ½ and ¼ inches in pile height. Polyethylene terephthalate (PET) and/or other yarn materials as well as other tufting configurations may additionally or alternatively be used. Using a 4 ply fiber may be beneficial in the sequestering of algae. Using an air-entangled yarn may provide bulk and structure that "grabs" the algae and easily releases by different methods of harvesting such as using flat ringers and orifice ringers. The release-ability of such an exemplary tufted fabric versus a woven fabric may be better due to tufted fabric and the yarn being the basis of the uptake as opposed to a woven structure base with fibers.

Figure 2:
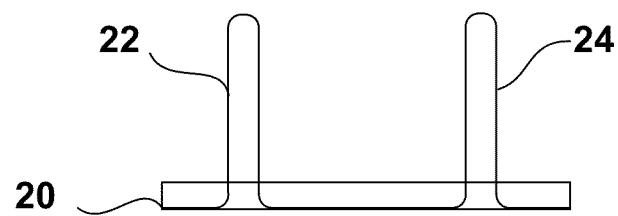
FIG. 2 is a side cross sectional view showing loop tufts of another exemplary tufted product according to embodiments of this invention.
Figure 3:
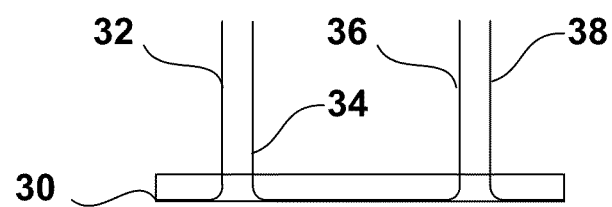
FIG. 3 is a side cross sectional view showing cut tufts of another exemplary tufted product according to embodiments of this invention.
Figure 4:
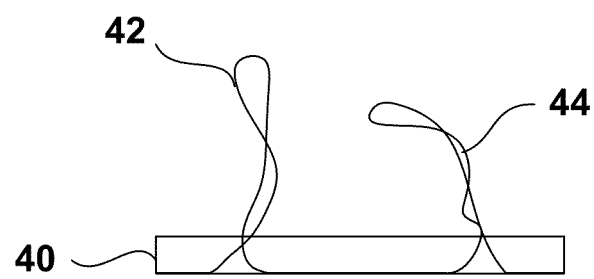
FIG. 4 is a side cross sectional view showing coiled tufts of another exemplary tufted product according to embodiments of this invention.

FIGS. 2-4 illustrate exemplary tufts of various types that may be used in a tufted product. FIG. 2 is a side cross sectional view showing loop tufts 22, 24 of another exemplary tufted product 20 configured to harvest algae. FIG. 3 is a side cross sectional view showing cut tufts 32, 34, 36, 38 of another exemplary tufted product 30 configured to harvest algae. FIG. 4 is a side cross sectional view showing coiled tufts 42, 44 of another exemplary tufted product 40 configured to harvest algae. The use of a coil yarn can provide benefits, for example, by providing invaginations that hold and protect attached algae and/or diatoms. A tufted product may comprise one or more different types of tufts, e.g., comprising both loops and cut loops.

A tufted product may be configured with high texture and/or other yarn characteristics that facilitate algae growth. High texture yarn, for example, may facilitate attachment of diatoms. High texture yarns may be formed by crimping and/or through the use of multiple filaments to provide increased surface area.

Certain embodiments involve a tufted product with yarn tufts spaced to balance the objective of providing increased surface area for algae growth and attachment with the objective of allowing water flow amongst the yarn tufts. Such spacing can be achieved by adjusting tufting machine gauge and stitch rate. For certain applications, spacing between yarns in the range of ⅛ inch to 2 inches is preferred, in the range of ¼ inch to 1.5 inches more preferred, and between ¼ inch and ¾ inch most preferred. In one exemplary product, approximately ½ inch spacing between yarn tufts was identified as providing an appropriate balance of increased surface area and water flow. On certain tufting machines, such spacing can be achieved using a ½ gauge and tufting at two stitches per inch. In certain circumstances, it may be advantageous to have more or less yarn along the length of a substrate than along the width of the substrate.

Certain embodiments involve a tufted product with tuft heights that improve algae growth and/or attachment. Yarn pile height may be varied through a substrate or substantially constant through the substrate. Generally, it is desirable that tuft height be high enough to allow attachment points for algae. Since it may be desirable to grow algae near the surface of the water for improved light exposure or for other reasons, it may be desirable to have the tufts of a tufted product near the surface of the water. However, it is generally desirable that tuft heights be limited to avoid or reduce tufts protruding above the water surface or otherwise cause a decrease in algae and diatom yield. In a flow-way embodiment in which water is periodically caused to flow across a substrate near the surface of the water, various pile heights may be appropriate. For certain applications, tuft heights in the range of ¼ inch to 2 inches are preferred, in the range of ½ inch to ⅜ inches more preferred, and between ¾ inch and ⅝ inch most preferred. In one exemplary product, approximately 1 inch tuft height was identified as providing an appropriate amount of surface area while keeping the yarn stem at or below the waterline.

Figure 5:
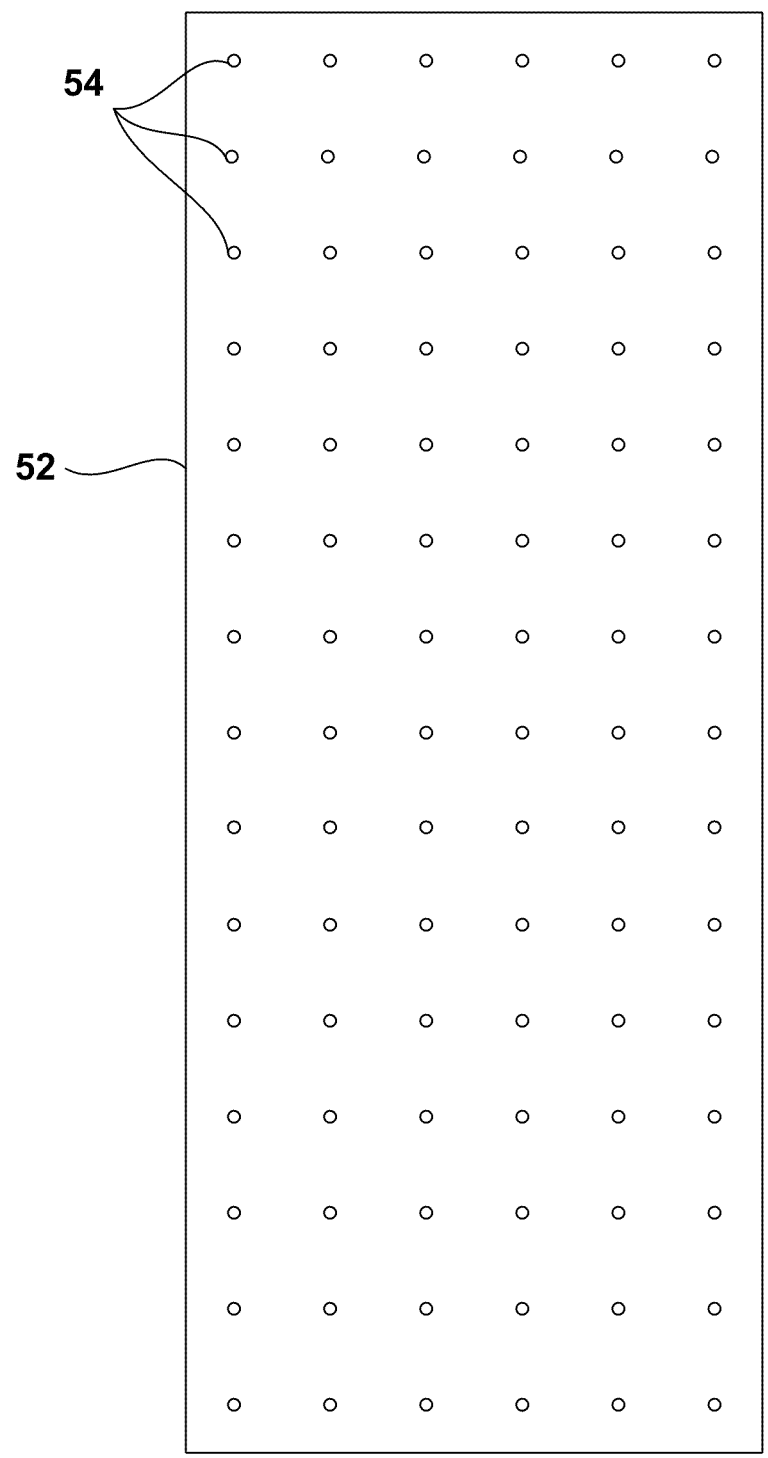
FIG. 5 is a top view showing a linear tufting pattern of another exemplary tufted product according to embodiments of this invention.

Other attributes of a tufted product can additionally or alternatively be configured to improve performance of the tufted product with respect to algae growth and otherwise. For example, the position of tufts within a substrate may be configured to achieve various objectives. In certain embodiments, tufts are formed in straight rows. FIG. 5 is a top view showing a linear tufting pattern of tufts 54 of another exemplary tufted product 52 configured to harvest algae. To avoid unnecessarily cluttering FIG. 5, only three of the many tufts 54 are marked with the numeral "54". It will be understood that the additional circles of FIG. 5 also depict locations of tufts in the tufted product 52.

Figure 6:
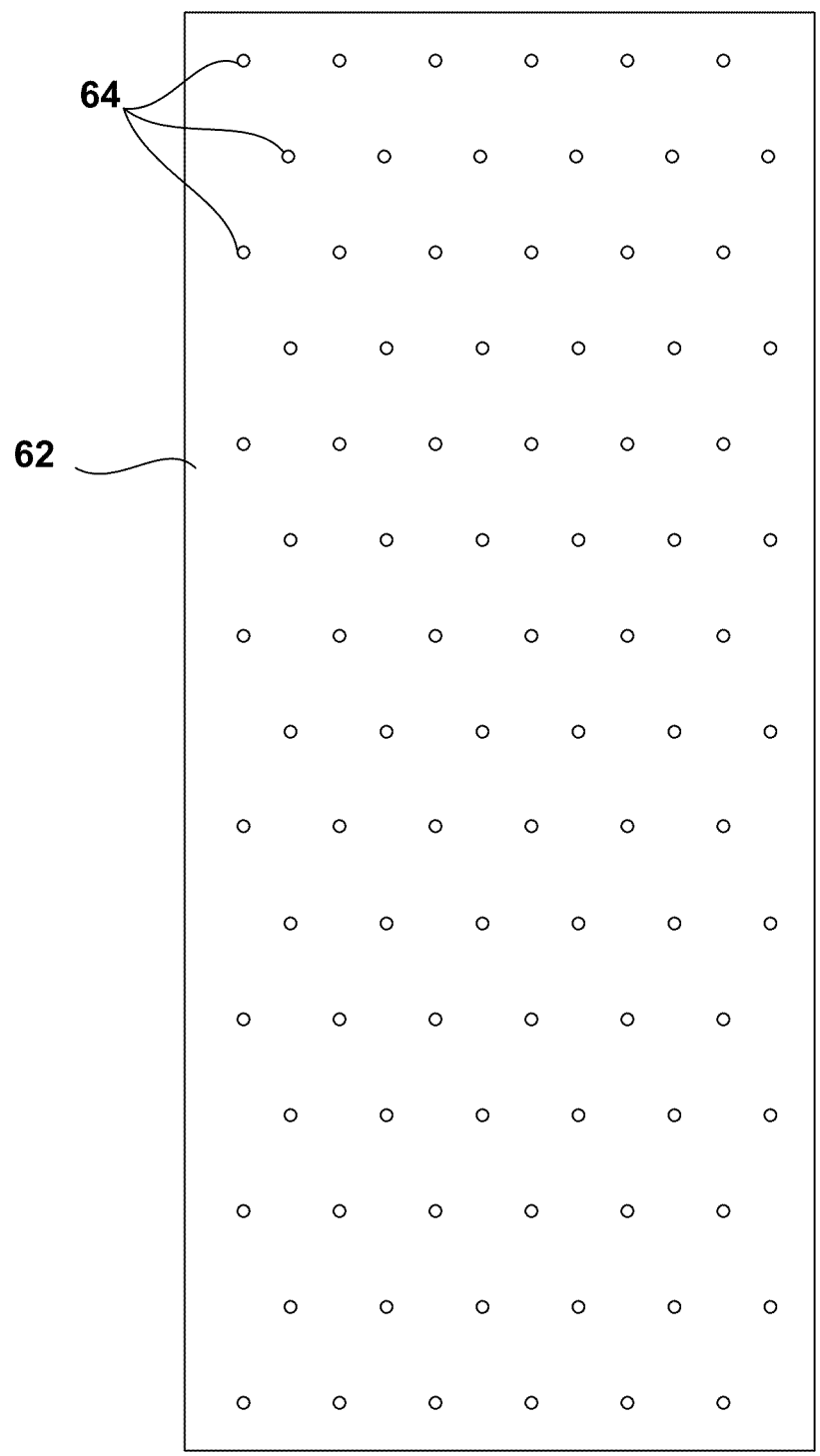
FIG. 6 is a top view showing a non-linear tufting pattern of another exemplary tufted product according to embodiments of this invention.

It may be desirable to shift a tufting machine's needle bars or to otherwise cause the formation of tufts in formations other than straight rows. FIG. 6 is a top view showing a non-linear tufting pattern of tufts 64 of another exemplary tufted product 62 configured to harvest algae. To avoid unnecessarily cluttering FIG. 6, only three of the many tufts 64 are marked with the numeral "64". It will be understood that the additional circles of FIG. 6 also depict locations of tufts in the tufted product 62. Such distortion of lineation can disrupt the flow or movement of water across or surrounding the tufted product 62. In the case of staggered rows, for example, water may have greater contact with tufts 64 and algae growing thereon.

In addition to the yarn texture characteristics, other yarn characteristics may also be configured to improve algae growth and attachment. As one example, yarn having a high luster may increase light reflection to facilitate or improve photosynthetic activity. As another example, continuous filament yarn may be selected to provide greater strength and/or minimize or eliminate loss of filaments associated with natural or stapled fibers. Such yarn may also improve product stability during a potentially disruptive algae harvesting process, for example, in which algae is mechanically scraped or pulled from the product.

Figure 7:
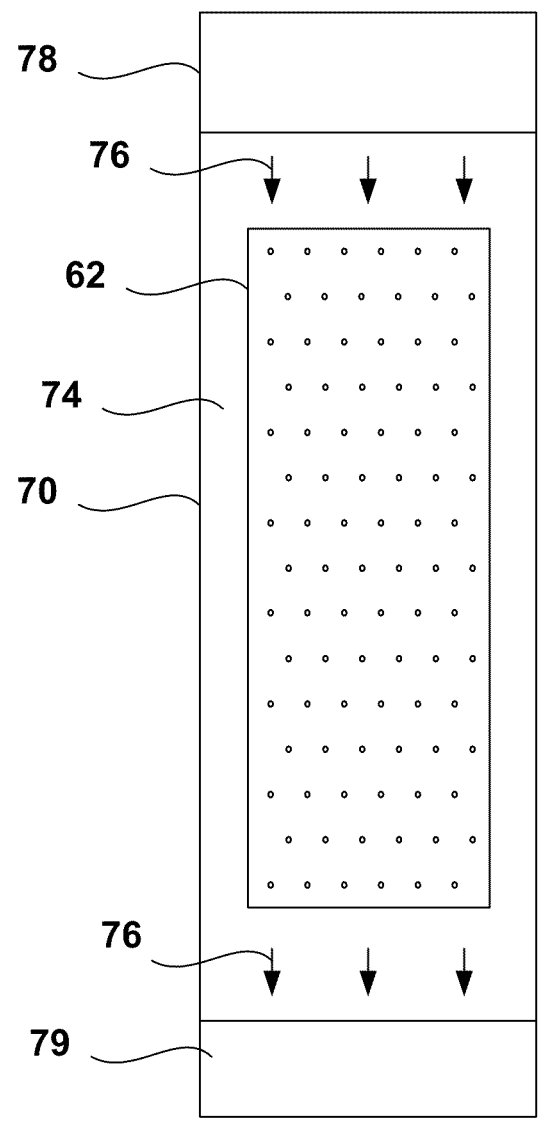
FIG. 7 is a top view showing a system for harvesting algae using the exemplary tufted product of FIG. 6.

FIG. 7 is a top view showing a system 70 for harvesting algae using the exemplary tufted product 62 of FIG. 6. The tufted product 62 is positioned submerged in water in trough 74. Water flows in the direction of arrows 76 from one end 78 of the trough to the other end 79 such that flowing water encounters tufts 64 of the tufted product 62 and promotes algal growth on the tufts 64. For example, water from a bay or other body of water may be taken from such a body of water and deposited in trough 74 for water remediation. In one exemplary configuration, trough 74 is 50 to 200 feet long and from 3 to 10 feet wide. The tufted product 62 is provided in the trough 74 to facilitate the growth of algae.

The tufted product 62 is provided near the surface of the water in the trough 74 along some of or most of the water surface area in the trough 74. Within such a trough 74, the water interacts with the tufted product that facilitates algae growth. The algae can help remove pollutants, produce biomass and oxygen, raise pH, and fix nitrogen. After a period of time, the water is returned to the bay or other body of water from which it was taken. A cable can be sewn in or otherwise attached to the edges of the tufted product to provide a mechanism for application and reel-up recovery after algal growth and remediation using, for example, winches.

Figure 8:
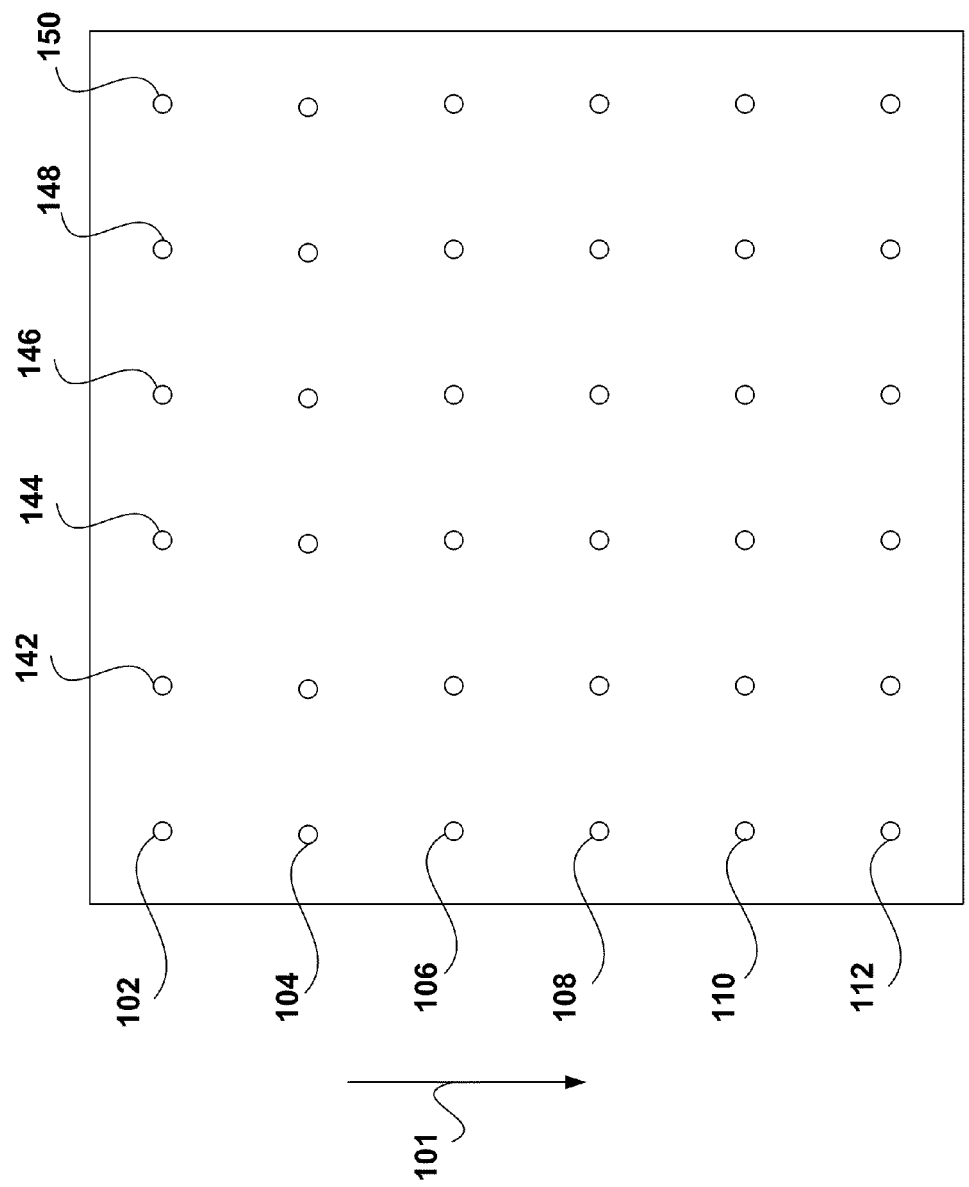
FIG. 8 is a top view showing a linear tufting pattern of a portion of the exemplary tufted product of FIG. 5.

FIGS. 8-10 are provided to illustrate the use of an exemplary tufted product in a system such as the system 70 of FIG. 7. FIG. 8 is a top view showing a linear tufting pattern of a portion of the exemplary tufted product 52 of FIG. 5. For illustrative purposes, positions of certain of the tufts 102, 104, 106, 108, 110, 112, 142, 144, 146, 148, 150 are identified. To avoid unnecessarily cluttering in FIG. 8, only some of the many tufts are marked with the numerals. It will be understood that the additional circles of FIG. 8 also depict locations of tufts in the tufted product 52. Arrow 101 depicts the direction of water flow that will be used in discussing an exemplary use of the tufted product 52 in FIGS. 9-10.

FIG. 9 is a side cross sectional view showing the portion of the exemplary tufted product 52 submerged in flowing water to facilitate algae growth. In FIG. 9, water flows in the direction of arrows 101 (only some arrows marked to avoid cluttering the Figure). The tufted product 52 is positioned, for example in trough 74 of FIG. 7, such that at least some of the water flows between the bottom 120 of trough 74 and tufted product 52. Similarly, tufted product 52 is positioned, for example in trough 74 of FIG. 7, such that water flows amongst the tufts 102, 104, 106, 108, 110, and 112, and, in this example, the tufts 102, 104, 106, 108, 110, and 112 are completely submerged and do not extend to or beyond the water surface 130.

FIG. 10 is another side cross sectional view showing the portion of the exemplary tufted product 52 submerged in flowing water to facilitate algae growth. In FIG. 9, water flows in a direction into the page. The tufted product 52 is positioned, for example in trough 74 of FIG. 7, such that at least some of the water flows between the bottom 120 and tufted product 52. Similarly, tufted product 52 is positioned, for example in trough 74 of FIG. 7, such that water flows amongst the tufts 102, 142, 144, 146, 148, 150, and, in this example, the tufts 102, 142, 144, 146, 148, 150 are completely submerged and do not extend to or beyond the water surface 130. FIG. 10 further illustrates openings 160, 170 in the tufted product 52 (not shown in the tufted product of FIG. 8 but similar to openings 214, 216, 218 in the embodiment of FIG. 11) that allow water to flow through the tufted product 52 to further promote algae growth.

In certain algae growing environments, water is taken from a bay or other body of water and provided to flow on or over a tufted product. In one example, the water flow submerges a tufted product approximately 1 inch in the water. Water can be provided continuously or can be periodically provided to allow the water to flow over the substrate in tidal-like manner. For example, water can be dropped or dumped into one end of a flow way causing water to flow down the length of the flow way to the other end at periodic time intervals. Intervals between such artificial water "tides" can vary depending on the particular algae, purpose of using the algae, and other factors.

For a system that uses a periodic water flow dump, an exemplary tufted product is formed using a tufting machine configured to tuft at ½ gauge at two stitches per inch with a ¼ inch shift step. A three-ply barber pile yarn with nylon 4 or nylon 6 bulked continuous filament (BCF), high twist, non-heat-set, high luster yarn is used to create tufts of approximately one inch pile height as measured after coiling where such tufts may have been tufted at 1.25 inch to 1.5 inch to achieve such a result. Such a product may have a face weight of approximately six ounces per square yard. This exemplary tufted product is tufted in a woven primary backing with a non-woven cap. Tufts are locked in with a hot melt application of 18 ounces+/−2 ounces for strength and tuft-bind. This specific configuration can be efficient with respect to providing surface area for growing algae, allowing nutrient flow, and production cost for certain algae applications.

Other products may change some or all of these configuration settings to achieve appropriate results in other circumstances. By way only of example, construction of the fabric may be modified in some applications to reduce attachment areas for crustaceans, mussels, etc. that may have a tendency to attach to the substrate and reduce algae growth by consuming what is feeding the algae and/or taking up room on the surface of the substrate that could otherwise be used for algae growth. For example, the non-woven cap may be omitted from the construction of the substrate if mussels are attracted and attach themselves to it, rendering it difficult to remove them after prolonged use.

In addition or alternatively, perforations or holes can be formed in a tufted product. For example, holes or perforations may be punched in a tufted product at various locations to allow $CO_2$ or other emissions for supporting algae growth. Perforation and/or holes can be achieved using spiked wheels, hole punch machines, or "cookie cutters," by selectively pulling out tufts to leave holes, or any other appropriate means. FIG. 11 is a front perspective view of a portion of another exemplary tufted product. The tufted product comprises coiled tufts 206, 208, 210, 212 tufted into a substrate 202 and secured by secondary backing 204. The tufted product further comprises openings 214, 216, 218 to allow water to flow through the substrate 202 and secondary backing 202 and thus through the tufted product to promote algae growth and/or harvesting.

In some embodiments, at least a portion of the tufted product has a positive charge characteristic to attract the algae, which has a negative charge, and thereby facilitate algae collection and/or growth on the product. By way only of example, the use of yarns (e.g., nylon, PET, etc.) having open dye sites having positive charge characteristics could be used. In use, the algae is attracted to such sites. In other embodiments, a conductive or antistat fiber (e.g., Shakespereare Isocor®, Thunderon®) is incorporated into at least one of the tufting primary, yarn, or tuft lock. In use, a positive charge is applied to the tufted product to facilitate attraction of the algae to the product.

Tufted products provided according to the techniques disclosed herein can facilitate the collection and/or growth of algae in other circumstances. As one example, a tufted product may be provided for use in an aquarium or other water tank. A tufted product may be connected on one, two, or more of its sides or otherwise configured to allow the product to grow algae in an open body of water. The product may periodically be collected for harvesting and then redeployed. An orifice ringer or other device can be used to remove algae from a tufted product.

As another example, a tufted product may be deployed or otherwise provided in a lake, bay, gulf, ocean, or other body of water to collect and remove algae from the body of water. The tufted product may be provided in such a body of water in various ways. For example, some or all of a tufted product may be provided in a body of water to allow the collection of algae on the tufted product while in the water, then removed from the water so that the collected algae can be removed from the tufted product, and then provided again into the body of water to again collect algae. A tufted product may be periodically or continuously moved, for example, in a large loop such that a portion of the product is immersed in the body of water collecting algae while collected algae on another portion of the product is being removed. A variety of techniques and systems for providing a tufted product to collect algae and then remove the collect algae are contemplated.

FIGS. 12-13 illustrate a tufted product 1202 used to reclaim algae from an algae-infested body of water 1204 to remediate the water in the body of water 1204 according to embodiments of this invention. The tufted product 1202 is provided in the form of a continuous loop that is positioned around a series of rollers 1206, 1208, 1210, 1212, 1214, 1216, 1218, 1220. At least one of the rollers is a drive roller to facilitate movement of the tufted product 1202 around the loop; other of the rollers may be free-spinning. In some embodiments, the tufted product is substantially flat as it moves through the body of water 1204 to maximize exposure to the body of water 1204 as it moves through it.

In the illustrated embodiments, the pile of the tufted product 1202 is oriented downwardly on the lower portion of the loop and oriented upwardly on the upper portion of the loop as the tufted product 1202 moves through the body of water 1204. However, the pile may be oriented in the opposite configuration if desired. The length of the loop (and thus that of the tufted product 1202) can be of any size to accommodate the dimensions of a particular body of water and/or other system configuration considerations.

Algae collects on the tufted product 1202 as it moves through the water. The tufted product 1202 encounters an algae collection apparatus which facilitates removal of the algae from the tufted product 1202. In some embodiments, the algae collection apparatus is nip rollers 1208, 1210 that squeeze or scrap the algae from the tufted product 1202. In other embodiments, the algae collection apparatus is a vacuum that sucks the algae from the tufted product 1202. Other suitable collection apparatus would be known to those of skill in the art and are contemplated herein. Finally, an algae repository 1228 is provided to collect the algae removed from the body of water 1204.

The disclosed embodiments are merely illustrative. In short, the techniques and the other features described herein have uses in a variety of contexts, not to be limited by the specific illustrations provided herein. The features shown are merely illustrative and are not intended to indicate that any component, feature, or method step is essential or necessary to any embodiment or limiting the scope of the present disclosure. The foregoing description of the embodiments has been presented only for the purpose of illustration and description and is not intended to be exhaustive or to limit the disclosure to the precise forms disclosed. Numerous modifications and adaptations are apparent to those skilled in the art without departing from the spirit and scope of the disclosure.

What is claimed is:

1. A product for growing or harvesting algae comprising:
a woven substrate; and
tufts tufted through the substrate, wherein the tufts are formed with nylon yarn and wherein spacing between adjacent tufts is at least 0.125 inches and wherein heights of the tufts are at least 0.25 inches.

2. The product of claim 1, wherein the substrate comprises woven polypropylene.

3. The product of claim 1, further comprising a polymer-based hot melt adhesive that provides dimensional stability and secures the tufts.

4. The product of claim 1 wherein the tufts are secured with a hot melt application of 18 ounces+/−2 ounces.

5. The product of claim 1 wherein a cable is attached to one or more edges of the substrate.

6. The product of claim 1 wherein heights of the tufts range from 1.25 inches to 1.5 inches inclusive, wherein the tufts are coiled such that heights of the tuft after coiling are approximately one inch.

7. The product of claim 1, wherein the tufts form non-linear rows.

8. The product of claim 1 wherein the substrate comprises a plurality of regularly-spaced openings.

9. The product of claim 1, wherein the substrate has a non-woven cap.

10. The product of claim 1, wherein the tufts comprise loops.

11. The product of claim 10, wherein the loops are coiled.

12. The product of claim 1, wherein the nylon yarn is air-entangled.

13. The product of claim 1, wherein the tufts are coiled.

14. The product of claim 1, wherein the nylon yarn comprises three or four plies.

15. The product of claim 1, wherein the nylon yarn comprises bulked continuous filament yarn.

* * * * *